United States Patent [19]

Ettare

[11] Patent Number: 4,542,750
[45] Date of Patent: Sep. 24, 1985

[54] NON-INVASIVE METHOD FOR DIAGNOSING INCIPIENT OR DEVELOPED CANCER TISSUE

[75] Inventor: Ross C. Ettare, Playa Del Rey, Calif.

[73] Assignee: Primary Diagnostic Systems, Inc., Santa Clara, Calif.

[21] Appl. No.: 408,179

[22] Filed: Aug. 13, 1982

[51] Int. Cl.$^4$ .............................................. A61B 5/00
[52] U.S. Cl. ................................... 128/760; 604/312; 436/64; 436/89
[58] Field of Search .............................. 128/759–760, 128/762, 749; 604/289–290, 312; 436/64, 89–90

[56] References Cited

U.S. PATENT DOCUMENTS

| | | | |
|---|---|---|---|
| 3,552,929 | 1/1971 | Fields et al. | 422/56 |
| 3,786,801 | 1/1974 | Sartorius | 128/760 |
| 3,902,847 | 9/1975 | Busch et al. | 436/86 |
| 4,059,404 | 11/1977 | Schuster et al. | 128/760 |
| 4,174,385 | 11/1979 | Reid | 424/1.1 |
| 4,190,056 | 2/1980 | Tapper et al. | 128/630 |
| 4,195,641 | 4/1980 | Joines et al. | 128/632 |
| 4,239,495 | 12/1980 | Gindler et al. | 436/86 |
| 4,260,777 | 4/1981 | Rittersdorf et al. | 549/33 |
| 4,270,924 | 6/1981 | Crooke et al. | 436/64 |
| 4,368,262 | 1/1983 | Bucovaz et al. | 435/23 |

OTHER PUBLICATIONS

Consden; "Qual. Analysis of Proteins: A Partition Chromatograhic Method Using Paper"; *Biochem. Journ.*, vol. 38, No .3, 5–1944, pp. 224–232.
Smith; "Colour Reactions on Paper Chromatograms by a Dipping Technique", *Nature*; vol. 171, No. 4340, 1-1953, pp. 43–44.
Dent; "Study of the Behav. of Some 60 Amino-Acids and Other Ninhydrin-Reacting Substances on Phenol--Collidine Filter Paper Chromatograms, W/Notes as to the Occurr. of Some of Them in Biol. Fluids"; *Paper Chromat. of Amino-Acids*, vol. 43, pp. 169–180.
Hamilton; "Amino-Acids on Hands", *Nature*, vol. 205, 1-1965, pp. 284–285.
Rothman et al., "Nitrogenous Mat'l on Normal Human Skin Surface", *Journal of Investigative Dermatology;* pp. 317–318.
Rothman et al.; "Amino-Acids on the Normal Human Skin Surface", *Journal of Investigative Dermatology;* pp. 319–321.
Roberts et al., "Distrib. of Free Amino-Acids in Mouse Epidermis in Various Phases of Growth as Determined by Paper Partition Chromatography"; *Science*, vol. 109, 1-1949, pp. 14–16.
Roberts et al., "Free Amino-Acids in Normal and Neoplastic Tissues of Mice as Studied by Paper Chromatography"; *Cancer Research*, pp. 645–648.
Roberts et al.; "Arginase Activ. and Nitrogen Content in Epidermal Carcinogenisis in Mice", *Cancer Research* 9, 1949, pp. 231–237.
Embden et al., "On the Presence of Serine in Human Perspiration"; Mun. Chem–Phys. Instit. and Med. Clin. of Mun. Hosp. in Frankfurt/Main, pp. 230–236.
Fukuda et al.; "Combined Protein and DNA Measurements by Ninhydrin-Schiff and Feulgen Tech."; *Histochemistry*, vol. 63, 1979, pp. 35–45.
Fujita et al.; "Improved Anal. for Urinary Polyamines by Use of High-Voltage Electrohoresis on Paper"; *Clin. Chem.* 26/11, 1980, pp. 1577–1582.
Recklies et al.; "Secretion of Proteinases from Malignant and Nonmalignant Human Breast Tissue", *Cancer Research;* 40; 3-1980, pp. 550–556.
Mairesse et al.; "Estrogen-Induced Synth. and Secretion of Proteins in the Human Breast Cancer Cellune MCF-7"; *Journ. of Steroid Biochem.* vol. 15, 1981, pp. 375–381.
Arklie et al.; "Differ. Antigens Expressed by Epithelial Cells in the Lactating Breast are also Detectable in Breast Cancers"; *Int. J. Cancer* 28, 1981, pp. 23–29.
Petrakis; "Genetic Cerumen Type; Breast Secretory Activ., and Breast Cancer Epidemiology"; *Genetics of Human Cancer*, pp. 297–300.
Nojiri; "Thin-Layer Chromatographic Studies on Malignolipin: On the Component of Malignolipin"; pp. 390–391.
Nojiri; "Thin-Layer Chromatographic Studies on Malignolipin: On Ninhydrin Positive Substance", pp. 401–406.
Petering et al.; "Isolation, Characterization, and Antigenicity of Malignolipin-Like Mat'l from Normal and Tumor Tissue"; *Cancer Research* 27, 1-1967; pp. 7–14.

*Primary Examiner*—Lee S. Cohen
*Assistant Examiner*—Angela D. Sykes
*Attorney, Agent, or Firm*—Limbach, Limbach & Sutton

[57] ABSTRACT

A diagnostic process is disclosed for detecting very early or developed stages of malignancy of tissue beneath a predetermined portion of the skin of a human patient. A sample of body secretion is obtained from the outer surface of the skin and is tested for presence of markedly decreased free, naturally occurring amino acids. The test has approximately the same order of sensitivity as a standard ninhydrin test. The diagnostic process of the invention is particularly adapted for mass screening of human females for early stages of breast cancer.

29 Claims, No Drawings

NON-INVASIVE METHOD FOR DIAGNOSING INCIPIENT OR DEVELOPED CANCER TISSUE

BACKGROUND OF THE INVENTION

1. Field of the Invention

The present invention is directed to a process for diagnosing malignancies. More particularly, the present invention is directed to a non-invasive process for detecting high risk, incipient, and developed cancer tissue from secretions collected from the skin overlying the tissue under examination.

2. Brief Description of the Prior Art

Several methods have been used in the prior art for diagnosing malignant cancerous tissue in various parts of the human body. As is well known, biopsy (excision) of a suspected cancerous tissue and subsequent histological examination of a section of the excised tissue usually provides information with substantial certainty about the malignancy or benign nature of the tissue under examination. In addition, x-ray examination usually also enables a physician to detect malignant tumors with substantial certainty. Still further, certain tumors such as tumors of the breast, may be detected by simple palpation, although the benign or malignant nature of a tumor must be confirmed by other methods.

Significant disadvantages of the prior art methods for diagnosing cancerous growth are the following. The prior art diagnostic methods are either uncertain (palpation), or invasive to the patient's body (biopsy). Even examination of a body portion suspected of cancer by X-ray is not without significant risk, because exposure to X-rays may have harmful effects and may even trigger cancerous growth. Furthermore, biopsy and X-ray examinations are procedures which require attention by highly trained medical personnel.

Thus it is apparent from the foregoing that neither biopsy nor X-ray examination is well suited for inexpensive mass screening of patients for detection of cancerous tissue. More particularly, neither biopsy nor X-ray examination is well suited for mass screening of female patients for breast cancer.

Another very significant disadvantage of prior art diagnostic methods for detection of cancer is that the prior art methods often fail to detect the cancer in its high risk, or developing stage.

Since the chances of curing a malignancy detected in its developing or incipient stage are significantly higher than curing a well developed or advanced cancer, it is clearly desirable to provide a method which is capable of detecting cancer in its early, incipient stage. It is further desirable to provide a inexpensive, non-invasive diagnostic test for cancer which is suitable for mass screening applications. However, the prior art has, by and large, failed to provide a diagnostic test satisfying the above-noted objectives.

SUMMARY OF THE INVENTION

In accordance with the foregoing, it is an object of the present invention to provide a diagnostic test for detecting an incipient or developed cancerous growth which is not invasive to the body of the patient and does not expose the patient to any risk associated with the test.

It is another object of the present invention to provide a diagnostic test for detecting an incipient or developed cancer, a test which is eminently suitable for mass screening applications.

It is still another object of the present invention to provide a non-invasive diagnostic test eminently suited for detecting an incipient breast cancer of a human patient.

It is a further object of the present invention to provide a non-invasive diagnostic test for detecting breast cancer in a human patient in a stage wherein the cancer is merely incipient, or can be characterized as a mere "high risk" of impending cancer.

These and other objects and advantages are attained by a diagnostic process wherein a sample of secretion is collected from a predetermined portion of the outer surface of the skin of a patient, said predetermined portion overlying the tissue being tested.

A solution of substantially known volume is derived from the collected sample. An aliquot of the solution is tested for presence or absence of free, naturally occurring amino acids in a test having substantially the same sensitivity as a standard ninhydrin test. Presence of free amino acids indicates a high porbability of freedom from underlying cancerous growth. Absence of free amino acids, as shown by the test, indicates presence of malignant cancerous growth in the tissue below the predetermined portion of the skin. Alternatively it indicates at least a high probability, or a high risk for incipient malignancy in the tissue.

The features of the present invention can be best understood together with further objects and advantages by reference to the following description.

DESCRIPTION OF THE PREFERRED EMBODIMENT

The following specification sets forth the preferred embodiment of the present invention in such a manner that any person skilled in the chemical and medical diagnostic arts can use the invention. The embodiment of the invention disclosed herein is the best mode contemplated by the inventor for carrying out his invention, although it should be understood that various modifications can be accomplished within the parameters of the present invention.

Thus, it has been discovered in accordance with the present invention that presence or absence of incipient or developed malignant growth may be diagnosed by testing secretions of the skin overlying the tissue under examination, for the presence of free, naturally occurring amino acids. Presence of free amino acids indicates healthy tissue. A marked decrease of detectable amounts of free amino acids indicates a high probability of existing malignancy, or an incipient stage of cancer. The incipient stage of cancer detectable by the process of the present invention may also be characterized as a "high risk" of impending cancer, or a "precancerous" state.

More particularly, it has been discovered in accordance with the present invention, that when a cancer grows or is about to begin to grow in a tissue which is substantially contiguous or the same with the tissue underlying the skin of a patient, then the overlying skin contains markedly reduced free amino acids as detected by the hereinafter described tests. On the other hand, normal skin overlying healthy tissue contains detectable amounts of free, naturally occurring amino acids.

In this regard, it is noted that the presence of free "protein building" alpha and other amino acids related thereto have been observed before in the prior art in body secretions. The following articles and publications indicate the state of the art with regards to free amino acids in cells, body secretions, and their correlation to malignant growth: E. Roberts et al., Science (1949) 109:14–16; E. Roberts et al., Cancer Res. (1949) 9:231–237; E. Roberts et al., Cancer Res. (1949) 9:645–648; G. Embden et al., Biochemische Z (1910) 28:230–236; S. Rothman et al., J. Invest. Dermat. (1949) 13:318–318; S. Rothman et al., J. Invest. Dermat. (1949) 13:319–321; R. Consden et al., Biochem. J. (1948) 43:169–180; C. Dent, Biochem J. (1948) 43:169–180; P. Hamilton, Nature (1965) 205:284–285; and I. Smith, Nature (1953) 171:43–44.

To the extent the above-noted articles and publications disclose the chemical structure of the amino acids and their derivatives which are found, for example, in normal human sweat, and other skin secretions, the subject matter of the above-noted articles is expressly incorporated herein by reference. By way of summary and for purpose of providing a clear background for the understanding and appreciation of the present invention, it is noted that the following "protein building" amino acids and related derivatives are found in a single wet human thumb print: taurine (0.001 μmole); urea (0.470 μmole); aspartic acid (0.023 μmole); threonine (0.018 μmole); serine (0.016 μmole); citrulline (0.004 μmole); glycine (0.071 μmole); glutamic acid (0.009 μmole); proline (0.011 μmole); alanine (0.029 μmole); -amino-n-butyric acid (less than 0.0001 μmole); valine (0.013 μmole); cystine (less than 0.0001 μmole); leucine (0.011 μmole); methionine (0.002 μmole); isoleucine (0.008 μmole; phenylalanine (0.007 μmole); ornithine (0.034 μmole); lysine (0.011 μmole); histidine (0.018 μmole); and arginine (0.005 μmole).

As is well known in the chemical and related arts, the above-noted amino acids are detectable by a substantially standard ninhydrin (or like) test, the chemical nature of which is so well established in the art that it need not be detailed herein.

Thus, returning now to the description of the present invention, samples of body secretion are taken of the outer surface of the skin which overlies the tissue to be examined. A solution, preferably aqueous solution, of substantially known volume is derived from the collected sample. This is most readily accomplished by evaporating the collected sample substantially to dryness, and thereafter dissolving the residue in a known volume of water. Thereafter, an aliquot of the solution is tested by the substantially standard ninhydrin (or like) test, for the presence of free amino acids. As was stated above, a negative ninhydrin test indicates the presence of malignant tissue. Perhaps even more importantly from a preventive diagnostic standpoint, a negative ninhydrin test indicates a precancerous, "high risk" state of the patient wherein onset of malignant growth is imminent.

Important aspects of the invention are that malignancies (or the very early stages thereof) can be detected by the invented process, where the tumor lies in a tissue contiguous or identical with the tissue disposed below the skin area of which the sample secretion is taken. Thus, breast cancer is readily detected by the invented process. In fact, the process of the invention is highly adapted for and primarily directed to mass screening of human females for incipient or developed breast cancer.

Another important aspect of the process of the present invention is that the test for presence or absence of free amino acids should have approximately the same order of magnitude of sensitivity for free amino acids as the herein specifically disclosed ninhydrin test. A well known and established isatin test also serves the purpose of the present invention. Many other, substantially equivalent tests are possible within the scope of the invention. However, the herein specifically described ninhydrin spot test has the specific advantage of being relatively simple, inexpensive and reliable. Therefore, it is well adapted for mass screening application.

Actual results obtained on patients screened for breast and other cancers indicate a very high degree of correlation between test results in the herein described diagnostic process (i.e. presence of markedly decreased free amino acids in the secretion) and histologically confirmed presence or absence of malignancy in the tissue under examination.

TABLE I

| Patient No. | Age | Histological Diagnosis | Test For Amino Acids Pos. | Test For Amino Acids Neg. | Interpretation Per Inv. | Path. Conf. |
|---|---|---|---|---|---|---|
| 1 | 63 | Mammary Dysplasia | X | | B | B |
| 2 | 75 | Wolfe's High Risk | | X | Ca | Ca |
| 3 | 53 | Infiltrative Carcinoma R-Breast | | X | Ca | Ca |
| 4 | 80 | Basal Cell Carcinoma, L-Clavicular Area | | X | Ca | Ca |
| 5 | 43 | L-Breast, No masses | X | | B | B |
| 6 | 43 | R-Breast, No masses | X | | B | B |
| 7 | 47 | Mass R-Breast-Fibrocystic Disease | X | | B | B |
| 8 | 47 | L-Breast, No mass palpated | X | | B | B |
| 9 | 37 | Malignant Melanoma R-Post Thigh | | X | Ca | Ca |
| 10 | 37 | R-Nasal Basal Cell Carcinoma | | X | Ca | Ca |
| 11 | 57 | Scirrhus Carcinoma R-Breast, Duct Carcinoma | | X | Ca | Ca |
| 12 | 53 | Periductal Fibrosis L-Breast | | X | High Risk | B |

B = Benign
Ca = Cancer
Path. Confirm. = Pathological Confirmation

The enclosed Table I indicates actual results, showing an arbitrarily assigned patient number, the respective age of the patient, histologically confirmed diagnosis of the patient, results of the diagnostic test of the present invention, and interpretation of the test. In this regard, it should be borne in mind that a "negative" test result means markedly decreased free amino acids, and therefore a "positive" indication of malignancy or high risk of the same.

Although exact explanation for the markedly decreased free amino acids on the skin overlying the cancerous tissue, or the tissue having a high risk for cancer, presently eludes medical science, the herein discovered correlation is probably connected with the high rate of metabolism and rapid growth of malignant cells. It is well appreciated that rapidly growing cells have a high requirement for amino acids. This may explain the markedly reduced "surplus" free alpha amino acids on the overlying skin.

The following specific example, which should be construed in an exemplary rather than limiting manner, sets forth the best mode for carrying out the process of the present invention.

EXAMPLE

Prior to testing, patients were asked to bathe the previous night and to not apply anything to their skin (e.g. perfume, deodorants, or powders, etc.).

Samples of amino acids were then obtained by wiping the breast or skin with distilled water-soaked cotton pledgets which were then placed in sterilized cups and stored in a freezer until ready for use. After defrosting, the sample was pipetted out from the cotton and collected in a beaker and the sample was then evaporated to dryness. The residue was redissolved in 3 ml of sterile deionized water and placed in a 5 ml vial. A total of 5 $\mu$l of sample was then spotted onto Whatman #1 chromatographic paper and allowed to dry (10-15 min.). Two drops of 0.25% ninhydrin in acetone (3 drops of 2% Pyridine is routinely incorporated immediately before use to deepen the resulting color) were then placed on the dried sample and allowed to dry again. Upon heating (@80° C. 3-5 min.) a purple color appeared and the color intensified by the next day, gradually fading within a week unless refrigerated. Ninhydrin-Cadmium Acetate may also be used as a reagent (0.2 g of Cadmium Acetate, 5 ml of Acetic Acid, 20 ml water—1 vol.; ninhydrin, 0.25% in Acetone—8 vol.). The latter produces a bright red-to-orange color with all amino acids. The colors are stable indefinitely. Isatin, still another reagent, gives a yellow color in the presence of amino acids.

As is apparent from the foregoing, significant advantages of the present invention include its simplicity, inexpensive nature, high degree of reliability, and ready adaptability for mass screening. Perhaps most importantly, the diagnostic process of the present invention has the advantage of being able to diagnose malignant growth in its incipient or "high risk" stage.

Since several modifications of the process of the present invention may become readily apparent to those skilled in the art in light of the above disclosure, the scope of the present invention should be interpreted solely from the following claims.

What is claimed is:

1. A process for determining the presence of a developed or incipient malignant tumor beneath a predetermined portion of the skin of a human being, said malignant tumor being located in a tissue substantially contiguous with the tissue underlying the predetermined portion of the skin, the process comprising the steps of:
   collecting a sample of secretion from an outer surface of the predetermined portion of the skin;
   testing at least an aliquot portion of the sample for the presence of free amino acids; and
   determining whether a malignant tumor is present based upon the quantity of said amino acids detected by said testing.

2. The process of claim 1 wherein the predetermined portion of the skin is on the breast of the human female.

3. The process of claim 1 wherein the step of collecting comprises wiping the predetermined portion of the skin with an object having at least limited capability for absorbing secretion.

4. The process of claim 3 wherein the object comprises cotton pledgets.

5. The process of claim 1 wherein the test comprises reacting an aliquot of a solution derived from the collected sample with a suitable chemical reagent capable of producing a visible color reaction with free naturally occurring alpha amino acids.

6. The process of claim 5 wherein the chemical reagent is selected from a group consisting of ninhydrin and isatin.

7. The process of claim 6 wherein the chemical reagent is ninhydrin.

8. The process of claim 7 wherein the test comprises the steps of depositing an aliquot of the solution derived from the collected sample in a predetermined area of a suitable absorbent medium, depositing a solution of ninhydrin on the absorbent medium in the predetermined area, and subsequently heating the medium.

9. A process for diagnosing the presence of incipient or developed malignancy below a predetermined portion of the skin of a human being in a tissue which is substantially contiguous with tissue underlying the predetermined skin portion, the process comprising the steps of:
   collecting a sample of secretion from the outer surface of the predetermined skin portion;
   obtaining a solution of substantially known volume from said sample;
   using an aliquot of a solution derived from the sample in a chemical test for free naturally occurring amino acids, said chemical test being of approximately the same sensitivity as a substantially standard ninhydran test; and
   determining whether an incipient or developed malignancy is present based upon the quantity of said amino acids detected in said test.

10. The process of claim 9 wherein the chemical test is a substantially standard ninhydrin test.

11. The process of claim 9 wherein the step of obtaining a solution further comprises the steps of evaporating the collected sample substantially to dryness to obtain a residue and dissolving said residue in a known volume of solvent to obtain a solution.

12. The process of claim 11 wherein the step of collecting comprises a step of wiping the predetermined skin portion with a suitable absorbent object.

13. A process according to claim 11 wherein the step of using an aliquot further comprises using an aliquot of known volume from said solution.

14. The process of claim 9 wherein the predetermined skin portion is at least a portion of the skin of a breast of the human female, and wherein the incipient or developed malignancy diagnosed is malignancy of breast tissue.

15. A process for diagnosing a developed or incipient cancerous breast tissue in a breast of a human female, said incipient cancerous tissue being identified as a high risk for cancer, the process comprising the steps of:
   collecting a sample of secretion from the outer surface of the skin of the breast;
   obtaining a solution of substantially known volume from said sample; and
   testing an aliquot of said solution for the presence of free naturally occurring amino acids.

16. The process of claim 15 wherein collecting the sample comprises the step of wiping the skin of the breast with a suitable absorbent object to absorb said secretions into the object.

17. The process of claim 16 wherein obtaining the solution comprises the steps of drawing the secretions from the object, evaporating said secretions to obtain a residue, and dissolving said residue in a suitable solvent.

18. The process of claim 17 wherein the step of testing comprises reacting the aliquot with a suitable test reagent for free amino acids.

19. The process of claim 18 wherein the test reagent is selected from a group consisting of ninhydrin, isatin, and cadmium acetate.

20. The process of claim 19 wherein the test reagent is ninhydrin.

21. The process of claim 20 wherein the step of testing comprises the step of depositing the aliquot on a suitable medium, depositing a solution of the ninhydrin reagent on the medium, and thereafter heating the medium.

22. A process for determining the presence of a developed or incipient malignant tumor beneath a predetermined portion of the skin, said malignant tumor being located in a tissue substantially contiguous with the tissue underlying the predetermined portion of the skin comprising the steps of
collecting a sample of secretion from an outer surface of the predetermined portion of the skin;
testing at least an aliquot portion of the sample for the presence of ninhydrin-reactive substance; and
determining whether a developed or incipient malignant tumor is present based upon the quantity of said ninhydrin-reactive substances detected by said testing.

23. A process according to claim 22 wherein the predetermined portion of the skin is on the breast of a human female.

24. A process according to claim 22 wherein the step of testing comprises reacting at least an aliquot of the sample with a chemical reagent capable of producing a visible color reaction with ninhydrin-reactive substances.

25. A process according to claim 22 wherein the chemical reagent is selected from a group consisting of ninhydrin and isatin.

26. A process according to claim 22 wherein the ninhydrin-reactive substances are comprised of amino acids.

27. A process according to claim 22 further including obtaining a solution of substantially known volume from said sample.

28. A process according to claim 27 wherein the step of obtaining a solution further comprises the steps of:
evaporating the collected sample substantially to dryness to obtain a residue; and
dissolving said residue in a known volume of a solvent to obtain a solution.

29. A process according to claim 28 wherein the step of testing an aliquot further comprises testing an aliquot of known volume from said solution.

* * * * *